June 5, 1951 J. D. BROWNELL Plant Pat. 1,015
ROSE PLANT
Filed March 13, 1950
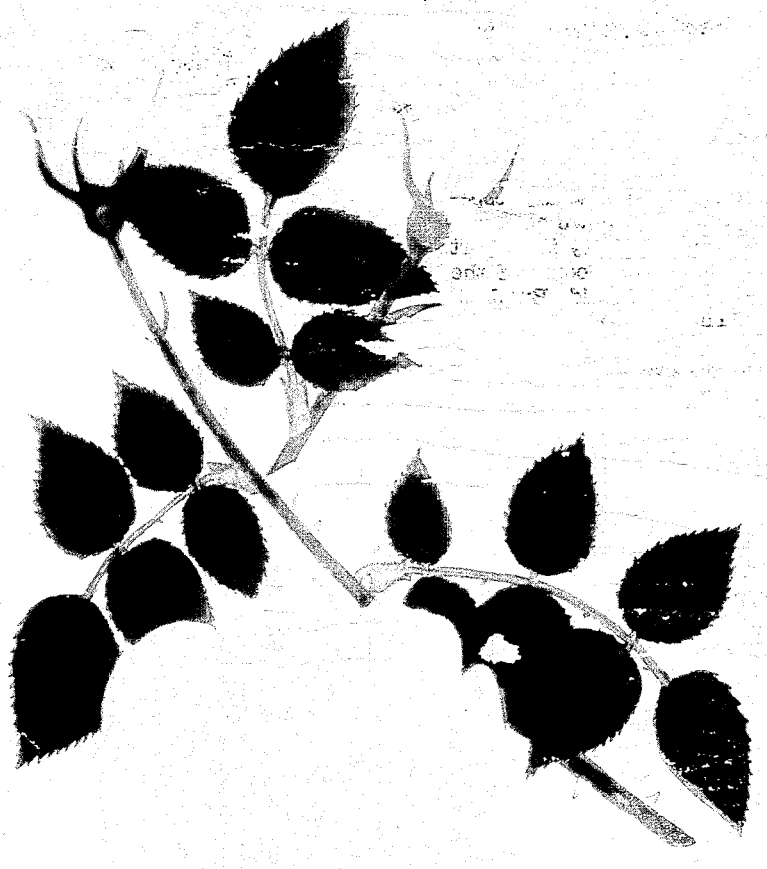
Josephine D. Brownell
INVENTOR.

Patented June 5, 1951

Plant Pat. 1,015

BEST AVAILABLE COPY

UNITED STATES PATENT OFFICE 1,015

ROSE PLANT

Josephine D. Brownell, Little Compton,

Application March 13, 1950, Serial No. 1

1 Claim. (Cl. 47—61)

My invention relates to rose plants and especially to the variety of the class known [illegible] cially as "hybrid teas." This variety [illegible] (or variation in the color of the bl[illegible] the *Rosa wichuraiana* hybrid tea hybrid, Break o' Day (not patented). This parent var[illegible] was produced by me. The color s[illegible] of this application, was discovered by [illegible] test and growing area of my breeding grounds in my research gardens at Little Compton, Rhode Island.

My new rose is [illegible] as to the following characteristics and especially as to their joint association with the characteristics inherited from *Rosa wichuraiana*, of hardiness or immunity from serious injury on account of cold temperatures prevailing in certain parts of the northern United States.

The "China Rose" shades (British Horticultural Chart) of its petals, in combination with the unique brilliance thereof and their tendency to hold these colors under exposure;

The novelty and variation within certain definite limits of the form of the bloom, its character of holding that form for a long time, and the petalage of the flowers;

Its character of fragrance;

Its unusual abundance of flowers, notably after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of [illegible] plants of *Rosa wichuraiana* of the dwarf reblooming type;

And especially its characteristic of partial freedom from premature defoliation by black-spot, under certain definite conditions of exposure, without any cultural control.

In the accompanying drawing forming a part of this specification I have shown my new rose in its natural colors, that is, as near as possible to do so artificially.

My new rose is otherwise described as follows:

Type: Hybrid tea, *Rosa wichuraiana* hybrid; dwarf, ascending, or tall; for garden display, cut flower and forcing or growing under glass.

Class: Hybrid tea crossed with *Rosa wichuraiana*, further restricted by me to include only those varieties that can survive moderately low sub-zero temperatures.

Breeding and discovery: This variety varied from its parent only as to color. The parent of this variety was produced and bred by me and under my direction by cross pollenation and subsequent propagation.

This variety was discovered by me on a hybrid tea type of bush on the 16th of September, 1947.

Plants of this variety budded from this sport onto *Rosa multiflora* root stock have, after being exposed to moderate sub-zero temperatures, survived and bloomed normally the following season in the hybrid tea manner. The variety has been propagated by budding at Little Compton, Rhode Island, in the months of July, August and September, in the years 1947–49, inclusive, and the characters have successively reproduced, true to the original sport.

The color of this variety varies in the pink shades of "China Rose," from 024/3 to 024/2, page 111 of British Horticultural Colour Chart, by R. F. Wilson (1941), dependent on exposure to sunlight and other environmental conditions.

All other essential information of this variety is set forth in the Plant Patent 696 of Climbing Break o'Day, excepting only the climbing habit described therein and the color of the petals thereof.

Comparisons: In comparison with its parent commercially known as Break o'Day (not patented) the plant characters are the same and the flower form and number of petals are the same but the color is different being the light shades of China Rose, in comparison with the color of Break o'Day which is pale Yellow Orange to Orange Buff overlaid with Grenadine Pink and Buff Yellow (ordinary dictionary definition).

In comparison with Climbing Break o'Day (Plant Patent No. 696) it compares similar to the above comparison.

In comparison with Pink Princess (Plant Patent No. 459) this variety is more of a self color of China Rose in comparison with the pink bicolor (ordinary dictionary definition) of Pink Princess and the formation of the center of the flower of the latter variety is more open centered and shows its pistils and stamens when fully open and this variety does not show its center when fully open.

BEST AVAILABLE COPY

In comparison with the variety in commerce known as "Early Morn" (not patented) the flower of that variety is very much lighter in color and the flower is more formal.

I know of no other *Rosa wichuraiana* hybrid tea hybrid comparable with this variety.

I claim:

The variety of hardy *Rosa wichuraiana* hybrid tea hybrid rose plant substantially as herein disclosed, characterized by the features of its parent variety Break o'Day except as to the color of the petals of the flower being China Rose pink.

JOSEPHINE D. BROWNELL.

REFERENCES CITED

The following references are of record in the file of this patent:

UNITED STATES PATENTS

| Number | Name | Date |
|---|---|---|
| Pl. Pt. 696 | Brownell | June 11, 1946 |

OTHER REFERENCES

McFarland, "Modern Roses III," published 1947, page 26 and pages 39 through 44.